United States Patent [19]

Von Der Saal et al.

[11] Patent Number: 4,870,077
[45] Date of Patent: Sep. 26, 1989

[54] HETEROCYCLIC SUBSTITUTED INDOLINONES

[75] Inventors: Wolfgang Von Der Saal, Weinheim; Walter-Gunar Friebe, Mannheim; Alfred Mertens, Schriesheim; Bernd Müller-Beckmann, Grünstadt; Lothar Kling, Mannheim, all of Fed. Rep. of Germany

[73] Assignee: Boehringer Mannheim GmbH, Mannheim, Fed. Rep. of Germany

[21] Appl. No.: 94,871

[22] Filed: Sep. 10, 1987

[30] Foreign Application Priority Data

Sep. 12, 1986 [DE] Fed. Rep. of Germany ....... 3631085

[51] Int. Cl.[4] .................. A61K 31/50; C07D 403/10; C07D 413/10; C07D 417/10
[52] U.S. Cl. ....................................... 514/254; 544/8; 544/68; 544/230; 544/182; 544/238; 548/265; 548/364; 548/410; 548/486
[58] Field of Search ................. 514/254; 544/238, 230

[56] References Cited

U.S. PATENT DOCUMENTS 4,617,302 10/1986 Robertson .......................... 514/254

FOREIGN PATENT DOCUMENTS 0068310 1/1983 European Pat. Off. .
0080296 6/1983 European Pat. Off. .
0155798 9/1985 European Pat. Off. .
0161918 11/1985 European Pat. Off. .
0178876 4/1986 European Pat. Off. .
223937 6/1987 European Pat. Off. ............ 544/238
2031404 4/1980 United Kingdom .

OTHER PUBLICATIONS

"Nomenclature of Organic Chemistry" (IUPAC, 1969), pp. 202–205.
NAKAO Chemical Abstracts; vol. 91, 5240p (1979).
Search Report and Abstract for EP259,871 (1987).

*Primary Examiner*—Mark L. Berch
*Attorney, Agent, or Firm*—Armstrong, Nikaido, Marmelstein, Kubovcik & Murray

[57] ABSTRACT

Heterocyclic substituted indolinones of the formula:

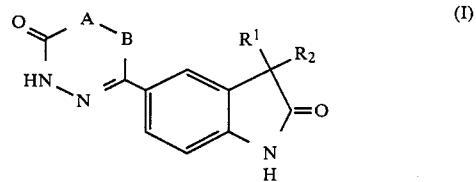

wherein $R_1$ is a hydrogen atom or an alkyl or hydroxyalkyl radical, $R_2$ is a carboxyl group or an alkoxy-carbonyl, hydroxyalkyl or alkylcarbonyloxyalkyl radical or $R_1$ and $R_2$, together with the carbon atom to which they are attached, form a lactone having 4, 5 or 6 ring atoms, A-B is $-CH_2-CH(R_3)-$, $-CH=CR_3-$, $-CH_2-NH-$, $-NH-CH_2-$, $-CH_2-O-$, $-O-CH_2-$, $-CH_2-S-$ or $-S-CH_2-$ radical, $R_3$ being a hydrogen atom or an alkyl or hydroxyalkyl radical, or A is a valency bond and B is a methylene radical

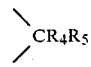

or an imino group

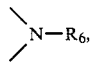

$R_4$, $R_5$, and $R_6$ independently being hydrogen atoms or alkyl radicals wherein the alkyl groups independently contain 1 to 6 carbon atoms; as well as the tautomers thereof and the physiologically acceptable salt thereof and the physiologically acceptable salts thereof with inorganic and organic acids, are disclosed, such as, for instance, the compound 5-(2,3,4,5-tetrahydro-3-oxopyridazin-6-yl)-3-ethoxycarbonyl-3-methyl-1H-indol n-2-one. The compounds of the invention are useful in the treatment of heart and circulatory diseases, for example, by producing a positive inotropic action in a patient to whom the compounds are administered.

13 Claims, No Drawings

HETEROCYCLIC SUBSTITUTED INDOLINONES

The present invention is concerned with new heterocyclic substituted indolinones, with processes for the preparation thereof and with pharmaceutical compositions containing them, as well as with intermediates for the preparation thereof.

The new heterocyclic substituted indolinones according to the present invention are compounds of the general formula:

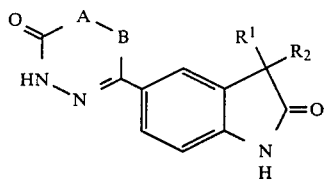 (I)

wherein $R_1$ is a hydrogen atom or an alkyl or hydroxyalkyl radical, $R_2$ is a carboxyl group or an alkoxycarbonyl, hydroxyalkyl or alkylcarbonyloxyalkyl radical or $R_1$ and $R_2$, together with the carbon atom to which they are attached, form a lactone, A–B is a —CH$_2$—CH(R$_3$)—, —CH=CR$_3$—, —CH$_2$—NH—, —NH—CH$_2$—, —CH$_2$—O—, —O—CH$_2$—, —CH$_2$—S— or —S—CH$_2$— radical, R$_3$ being a hydrogen atom or an alkyl or hydroxyalkyl radical, or wherein A is a valency bond and B is a methylene radical

or an imino group

$R_4$, $R_5$ and $R_6$ being hydrogen atoms or alkyl radicals; as well as the tautomers thereof and the physiologically acceptable salts thereof with inorganic and organic acids.

The compounds of general formula (I) contain at least one asymmetric carbon atom. Thus the present invention also includes the optically-active forms and the racemic mixtures of these compounds.

The positive inotropic action of compounds of general formula (I) in which $R_1$ has the above-given meaning and $R_2$ is a hydrogen atom or a methyl radical or in which $R_1$ and $R_2$ together form a cyclopropane ring and A–B signifies a —CH$_2$—C(R$_3$)— or —CH=CH(R$_3$)— radical, are already known from European Patent Specification Nos. 0,155,798; 0,161,918 and 0,178,876. Surprisingly, we have now found that compounds of general formula (I), in which $R_2$ and A–B have the above-given meanings, also display an outstanding heart-power increasing action. Furthermore, the compounds of general formula (I) have a blood pressure-reducing action and/or improve the microcirculation and influence the thrombocyte function.

When $R_1$ signifies an alkyl or hydroxyalkyl radical, then straight-chained or branched alkyl chains with up to 6 carbon atoms are preferred, especially the methyl, ethyl, propyl and hydroxymethyl radicals.

When $R_2$ signifies an alkoxycarbonyl, hydroxyalkyl or alkylcarbonyloxyalkyl radical, then the straight-chained or branched alkyl radicals preferably contain up to 6 carbon atoms, preferred radicals including the methoxycarbonyl, ethoxycarbonyl, isopropoxycarbonyl, tert.-butoxycarbonyl, hydroxymethyl and methylcarboxymethyl radicals.

When $R_1$ and $R_2$ together form a lactone ring, then a ring with 4, 5 or 6 members is preferred, especially the γ-butyrolactone ring.

When A–B forms one of the above-mentioned groups in which $R_3$ signifies an alkyl or hydroxyalkyl radical, then alkyl radicals with up to 3 carbon atoms are preferred, especially the methyl radical.

When A signifies a valency bond and B a

or

radical, $R_4$, $R_5$ and $R_6$ being alkyl radicals, then alkyl radicals containing up to 3 carbon atoms are preferred, especially the methyl radical.

Especially preferred compounds of general formula (I) are those in which $R_1$ is a methyl, ethyl or propyl radical, $R_2$ is a methoxycarbonyl, ethoxycarbon, isopropoxycarbonyl, tert.-butoxycarbonyl, hydroxymethyl or methylcarboxymethyl radical or $R_1$ and $R_2$, together with the carbon atom to which they are attached, represents a γ-butyrolactone ring, A–B is a —CH$_2$—CH$_2$—, —CH=CH—, —CH$_2$—CH(CH$_3$)—, —CH$_2$—CH(CH$_2$OH)—, —CH=C(CH$_3$)—, —O—CH$_2$— or —HN—CH$_2$— radical and A is a valency bond and B is a —C(CH$_3$)$_2$— radical.

The compounds of general formula (I) can be prepared by known processes. However, the processes indicated by the following schemes a–e are especially advantageous:

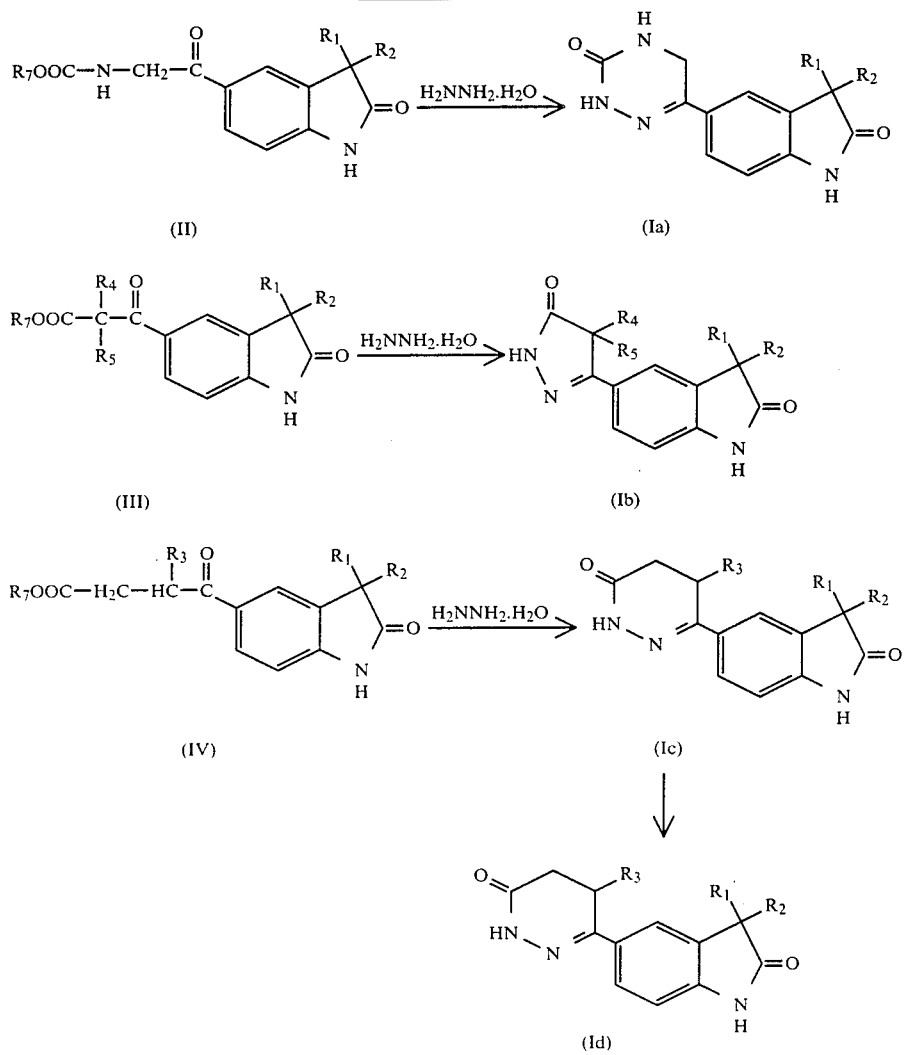

As shown in scheme a, some of the compounds of general formula (I) can be prepared by reacting ketocarboxylic acid derivatives of general formulae (II), (III) and (IV) with hydrazine hydrate. These include compounds of general formula (I), wherein $R_1$ and $R_2$ have the given meanings and A-B is either a —NH—$CH_2$— radical (formula Ia) or a —$CH_2$—$CH(R_3)$— radical (formula Ic) or in which A is a valency bond and B is a

radical (formula Ib), $R_3$, $R_4$ and $R_5$ having the above-given meanings. In the compounds of general formula (II), (III) and (IV), $R_1$, $R_2$, $R_3$ and $R_5$ have the above-given meanings and $R_7$ is a hydrogen atom or a lower alkyl radical, such as a methyl or ethyl radical, or a phenyl radical.

The reactions of compounds (II) to compounds (Ia), of compounds (III) to compounds (Ib) and of compounds (IV) to compounds (Ic) preferably take place in a solvent, for example ethanol or isopropanol, or in a mixture, for example isopropanol/water, in the presence of 1 to 5 moles and preferably of 1 or 2 moles of hydrazine hydrate, at a temperature of from ambient temperature to the boiling point of the solvent or solvent mixture used.

Compounds of general formula (I), wherein $R_1$, $R_2$ have the above-given meanings and A-B is a —$CH_2$—$CHR_3$— radical (formula Ic), can, if desired, subsequently be oxidised to compounds of general formula (I), in which A-B is a —CH=$CR_3$— radical (formula Id). This can be carried out by bromination/dehydrobromination by a noble metal-catalysed dehydrogenation or by oxidation with pyrolusite or m-nitrobenzenesulphonic acid (cf. J. med. Chem., 17, 273/1974).

Scheme b:

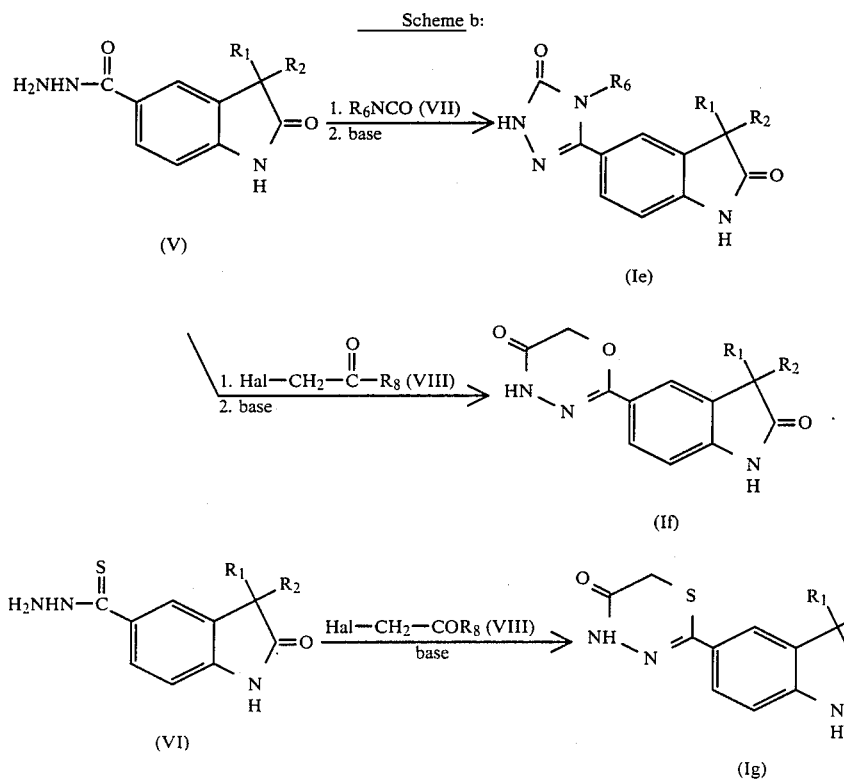

As scheme b shows, some of the compounds of general formula (I) can be prepared by reacting hydrazides of general formulae (V) or (VI) with isocyanates of general formula (VIII) or with halocarboxylic acids of general formula (VIII) in the presence of bases. This concerns those compounds of general formula (I) in which $R_1$ and $R_2$ have the above-given meanings and A-B is either a —$CH_2$—O— radical (formula If) or a —$CH_2$—S— radical (formula Ig) or in which A is a valency bond and B is an imino group $$\diagdown_{N R_6} \diagup$$

(formula Ie). In the isocyanates of general formula (VII), $R_6$ has the above-given meaning. In the haloacetic acids of general formula (VIII), Hal is a halogen atom, for example a chlorine, bromine or iodine atom but preferably a chlorine atom, and $R_8$ is a halogen atom, preferably a chlorine atom, or an alkoxy radical, preferably a methoxy or ethoxy radical.

The syntheses of compounds of general formula (Ie) and (If) are preferably carried out in two stages. In the first stage, a hydrazide of general formula (V) is reacted either with an isocyanate of general formula (VII) or with a halocarboxylic acid of general formula (VIII), preferably in an inert solvent, for example toluene or dioxan, and in the presence of a base, such as potassium carbonate. In both cases, as intermediate products, there are obtained diacyl hydrazines which are then reacted in a dipolar aprotic solvent, for example dimethylformamide, with a base, for example sodium hydride, or with an alkali metal carbonate in acetone. This stage is preferably carried out at an elevated temperature, for example at about 100° C., the compounds of general formulae (Ie) or (If) being obtained directly.

The reaction of the thiohydrazides of general formula (VI) to give compounds of general formula (Ig) is preferably carried out in one stage. In this case, it is preferred to use an activated derivative of a halocarboxylic acid of general formula (VIII), for example a methyl or ethyl ester. The reaction is preferably carried out in aqueous solution at ambient temperature in the presence of a base, for example sodium hydroxide.

Scheme c:

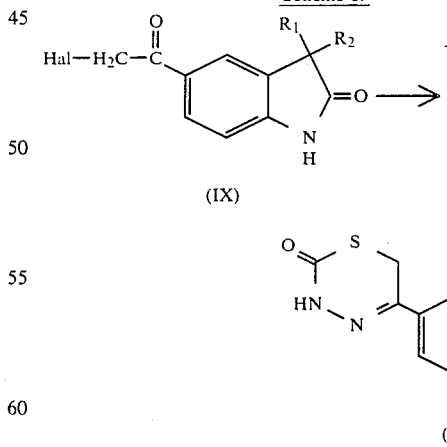

Compounds of general formula (I), wherein $R_1$ and $R_2$ have the above-given meanings and A-B is a —S—$CH_2$— radical (formula Ih), are preferably prepared by reacting compounds of general formula (IX) with ethyl thiocarbazate or with methyl thiocarbazate. The reaction is caried out in an organic solvent, preferably in acetonitrile or ethanol, at an elevated temperature and preferably at the boiling point of the solvent used.

Scheme d:

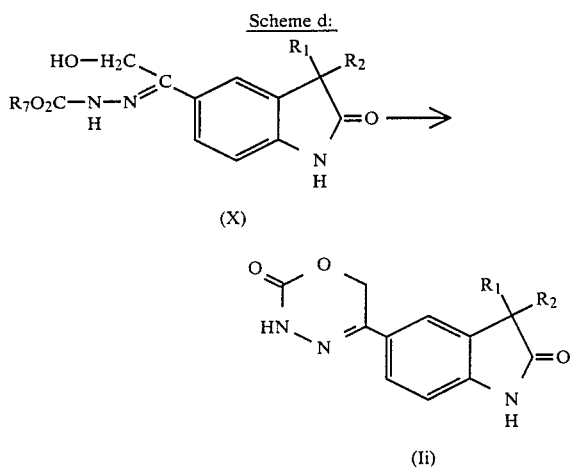

Compounds of general formula (I), wherein $R_1$ and $R_2$ have the above-given meanings and A-B is a $-O-CH_2-$ radical (formula Ii), are prepared by cyclising hydrazones of general formula (X), wherein $R_1$, $R_2$ and $R_7$ have the above-given meanings.

The cyclisation is preferably carried out in the presence of a base, for example sodium methylate, in a solvent, for example ethanol, at ambient temperature.

Scheme e:

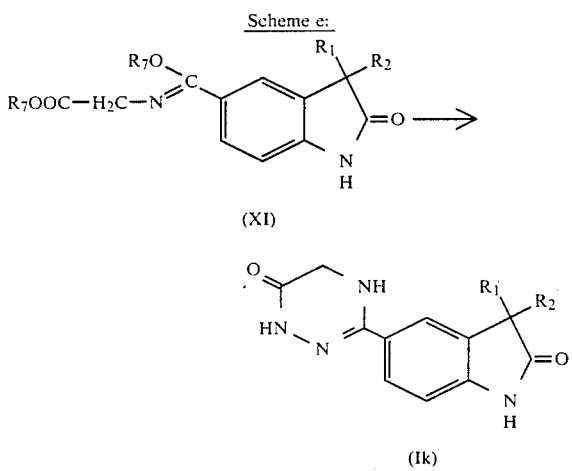

Compounds of general formula (I), wherein $R_1$ and $R_2$ have the above-given meanings and A-B is a $-CH_2-NH-$ radical (formula Ik), are prepared from imino ethers of general formula (XI), wherein $R_1$, $R_2$ and $R_7$ have the above-given meanings, by reaction with hydrazine hydrate. This reaction is preferably carried out in a solvent, for example ethanol, at a temperature up to the boiling point of the solvent.

The compounds of general formula (I) can also be subsequently converted into other compounds of general formula (I).

This applies to the reduction of compounds of general formula (I), wherein $R_1$ and A-B have the above-given meanings and $R_2$ is an ester group, to give those compounds of general formula (I), wherein $R_2$ is a hydroxymethyl radical. This reduction is preferably carried out by the use of lithium aluminium hydride in an inert solvent.

This also applies to the esterification of compounds of general formula (I), wherein $R_1$ and A-B have the above-given meanings and $R_2$ is a hydroxyalkyl radical, to give compounds of general formula (I), wherein $R_2$ is an alkylcarbonyloxyalkyl radical.

Furthermore, this applies to the esterification of compounds of general formula (I), wherein $R_1$ and A-B have the above-given meanings and $R_2$ is a carboxyl group, to give those compounds of general formula (I), wherein $R_2$ is alkoxycarbonyl radical. The said esterifications are carried out by methods known from the literature.

In addition, this applies to the hydrolysis and alcoholysis of compounds of general formula (I), wherein $R_1$ and A-B have the above-given meanings and $R_2$ is an alkoxycarbonyl radical, to give those compounds of general formula (I), wherein $R_2$ is a carboxyl group (saponification) or an alkoxycarbonyl radical (transesterification). The saponifications and transesterifications are carried out by processes known from the literature.

The starting materials of general formula (II), (III), (IV), (V), (VI), (IX), (X) and (XI) required for reaction schemes a–3 are also new and the subject of the present invention.

The preparation thereof takes place via a Friedel-Crafts reaction between acid halides or anhydrides and oxindoles of the general formula:

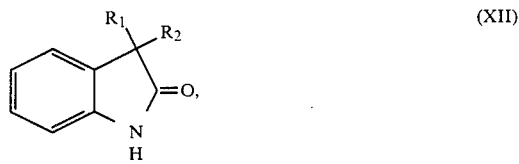

wherein $R_1$ and $R_2$ have the above-given meanings.

The compounds of general formula (XII) are either known from the literature or can be prepared by processes known from the literature (cf. R. M. Acheson et al., J. Chem. Soc., Perkin I, 1979, 595).

By the reaction of compounds of general formula (XII) with ester chlorides of the general formula:

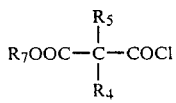

wherein $R_4$, $R_5$ and $R_7$ have the above-given meanings, there are obtained compounds of general formula (III), by reaction with ester chlorides of the general formula:

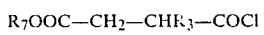

wherein $R_2$, $R_3$ and $R_7$ have the above-given meanings, there are obtained compounds of general formula (IV), by reaction with haloacetic acid chlorides, there are obtained compounds of general formula (IX) and by reaction with acetyl chlorides, there are obtained compounds of the general formula:

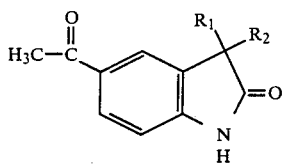
(XIII)

wherein $R_1$ and $R_2$ have the above-given meanings.
These Friedel-Crafts reactions are carried out in a solvent, for example carbon disulphide, methylene chloride, dichloroethane or nitrobenzene, in the presence of an excess of a Lewis acid, for example aluminium chloride or aluminium bromide, at a temperature of from 0° to 150° C. and preferably at the boiling point of the solvent or in the presence of a large excess of up to 10 mole of aluminium chloride in dimethylformamide at a temperature of from 0° to 150° C.

The compounds of general formula (II) required as starting materials are obtainable in two stages from compounds of general formula (IX):

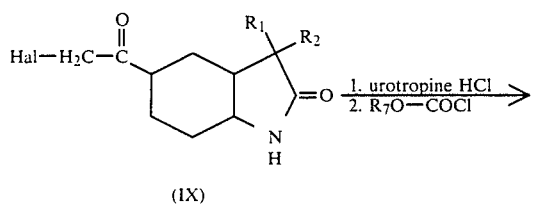
(IX)

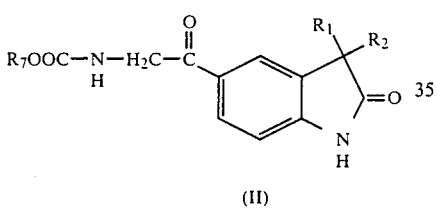
(II)

By reaction of compounds of general formula (IX) with urotropine and subsequent acid hydrolysis, there are obtained α-aminoketones which are acylated on the nitrogen atom with chloroformic acid esters and the compounds of general formula (II) thus obtained (cf. European Patent Specification No. 0,080,296).

The other compounds required as starting materials can be obtained from compounds of general formula (XIII).

Thus, compounds of general formula (V) are obtained by subjecting compounds of general formula (XIII) to a haloform reaction, the acetyl radical thereby being oxidised by hypochlorite or hypobromite to give the acid and subsequently with hydrazine hydrate. These compounds are, in turn, reacted with sulphur-transferring reagents to give compounds of general formula (VI), which are also required as starting materials:

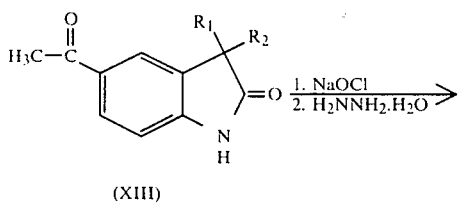
(XIII)

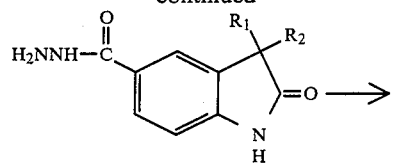
(V)

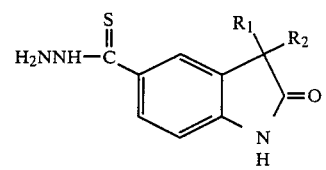
(VI)

The carboxylic acids obtained by the hypochlorite reaction of compounds of general formula (XIII) also serve for the preparation of imino ethers of general formula (XI). This takes place by alkylation of the amides by means of trialkyl oxonium salts (cf. Perst. Oxonium Ions in Organic Chemistry, pp. 128–137, Verlag Chemie, 1971).

If, on the other hand, compounds of general formula (XIII) are oxidised with a milder oxidation agent, preferably with iodobenzene-diacetate, then α-hydroxyketones can be obtained which are reacted with alkyl carbazates to give compounds of general formula (X) required as starting materials (cf. European Patent Specification No. 0,080,296):

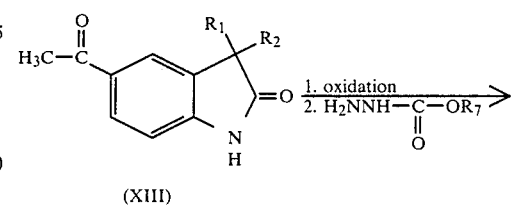
(XIII)

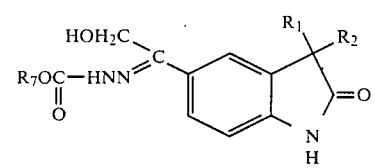

Furthermore, the compounds obtained of general formula (I) can, if desired, subsequently be converted into the physiologically acceptable acid addition salts thereof with inorganic and organic acids. As acids for this prupose, there can be used, for example, hydrochloric acid, hydrobromic acid, sulphuric acid, phosphoric acid, fumaric acid, succinic acid, tartaric acid, citric acid, lactic acid, maleic acid or methanesulphonic acid.

As already mentioned hereinbefore, the new compounds of general formula (I), the tautomers thereof and the physiologically-acceptable salts thereof display, in the case of a long period of action, superior pharmacological properties, especially a blood pressure-lowering and/or positive inotropic action and/or influence the thrombocyte function and improve the microcirculation.

For the preparation of pharmaceutical compositions, the compounds of general formula (I) are mixed in known manner with appropriate pharmaceutical carrier materials, aroma, flavouring and colouring materials and formed, for example, into tablets or dragees or, with the addition of appropriate adjuvants, suspended or dissolved in water or an oil, for example olive oil.

The new compounds according to the present invention of general formula (I) and the salts thereof can be administered in liquid or solid form enterally or parenterally. As injection medium, it is preferred to use water which contains the additives usual in the case of injection solutions, such as stabilising agents, solubilising agents and/or buffers.

Such additives include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (cuch as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and/or sweetening agents.

The compounds according to the present invention are usually administered in amounts of 10 to 500 mg. per day, referred to a body weight of 75 kg. It is preferred to give 1 to 2 tablets with an active material content of 5 to 200 mg. 2 or 3 times a day. The tablets can also be retarded so that 1 to 2 tablets with 10 to 500 mg. of active material only have to be given once per day. The active materials can also be given by injection 1 to 8 times a day or by continuous infusion, in which case amounts of 5 to 200 mg. per day normally suffice.

Preferred according to the present invention are, apart from the compounds described in the Examples, also the following compounds and the tautomers thereof:

5-(2,3,4,5-tetrahydro-3-oxopyridazin-6-yl)-3-tert.-butyloxycarbonyl-3-methyl-1H-indolin-2-one 5-(2,3,4,5-tetrahydro-3-oxopyridazin-6-yl)-3-hydroxymethyl-3-methyl-1H-indolin-2-one 5-(2,3,4,5-tetrahydro-3-oxopyridazin-6-yl)-3-methylcarbonyloxymethyl-3-methyl-1H-indolin-2-one 5'-(2,3,4,5-tetrahydro-3-oxopyridazin-6-yl)-spiro[tetrahydrofuran-2-one-3,3'-indolin-2'-one]

5-(5-methyl-2,3,4,5-tetrahydro-3-oxopyridazin-6-yl)-3-methyl-3-ethoxycarbonyl-1H-indolin-2-one 5-(5-hydroxymethyl-2,3,4,5-tetrahydro-3-oxopyridazin-6-yl)-3-methyl-3-ethoxycarbonyl-1H-indolin-2-one 5-(2,3-dihydro-2-oxo-6H-1,3,4-oxodiazin-5-yl)-3-ethoxycarbonyl-3-methyl-1H-indolin-2-one 5-(2,3,4,5-tetrahydro-3-oxo-1,2,4-triazin-6-yl)-3-ethoxycarbonyl-3-methyl-1H-indolin-2-one 5-(3,4-dihydro-2H-4,4-dimethyl-3-oxopyrazol-5-yl)-3-ethoxycarbonyl-3-methyl-1H-indolin-2-one.

Preferred precursors in the meaning of the present invention (general formulae II, III, IV, V VI, IX, X and XI) are, apart from those mentioned in the Examples, also the following:

5-(ethoxycarbonylaminoacetyl)-3-ethoxycarbonyl-3-methylindolin-2-one 5-(2-ethoxycarbonyl-2-methylpropionyl)-3-ethoxycarbonyl-3-methylindolin-2-one 5-(3-ethoxycarbonyl-2-hydroxymethylpropionyl)-3-ethoxycarbonyl-3-methylindolin-2-one 5-hydrazinocarbonyl-3-ethoxycarbonyl-3-methylindolin-2-one 5-hydrazinothiocarbonyl-3-ethoxycarbonyl-3-methylindolin-2-one 5-(hydroxyacetylethoxycarbonylhydrazone)-3-ethoxycarbonyl-3-methylindolin-2-one 5-(3-methoxycarbonylpropionyl)-3-methoxycarbonyl-3-methylindolin-2-one 5-(3-methoxycarbonylpropionyl)-3-ethoxycarbonyl-3-propylindolin-2-one 5-(3-methoxycarbonylpropionyl)-3-isopropyloxycarbonyl-3-methylindolin-2-one 5-(3-methoxycarbonylpropionyl)-3-tert.-butyloxycarbonyl-3-methylindolin-2-one 5-chloromethylcarbonyl-3-ethoxycarbonyl-3-ethoxycarbonyl-3-methyl-1H-indolin-2-one 5-(ethoxycarbonylethoxycarbonylmethylimine)-3-ethoxycarbonyl-3-methyl-1H-indolin-2-one.

The following Examples are given for the purpose of illustrating the present invention:

EXAMPLE 1

5-(2,3,4,5-Tetrahydro-3-oxopyridazin-6-yl)-3-ethoxycarbonyl-3-methyl-1H-indolin-2-one 0.34 ml. (7.2 mMole) hydrazine hydrate are added to 2.4 g. (7.2 mMole) 3-ethoxycarbonyl-3-methyl-5-(3-methoxycarbonylpropionyl)-1H-indolin-2-one in 50 ml. ethanol and heated overnight under reflux. After cooling, the reaction mixture is filtered. There is isolated 1.4 g. of the title compound (62% of theory); m.p. 274°–276° C.

The 3-ethoxycarbonyl-3-methyl-5-(3-methoxycarbonylpropionyl)-1H-indolin-2-one used as starting material is prepared in the following way: 3.4 ml. 27 mMole) 3-methoxycarbonylpropionyl chloride are added dropwise at 15° to 20° C. to a mixture of 12.1 g. (85 mMole) aluminium chloride and 40 ml. carbon disulphide and subsequently a solution of 5.0 g. (23 mMole) 3-ethoxycarbonyl-3-methyloxindole in 10 ml. carbon disulphide and 5 ml. dichloromethane. The reaction mixture is stirred for 20 hours at ambient temperature and the solution is decanted off. The resinous residue is decomposed with ice and extracted with dichloromethane. After chromatography on silica gel (elution agent: dichloromethane/methanol 99:1 v/v), there are obtained, besides 2.4 g. of unreacted 3-ethoxycarbonyl-3-methyloxindole, 2.9 g. of the desired product (38% of theory); m.p. 107°–109° C.

EXAMPLE 2

In a manner analogous to that described in Example 1, there is obtained 5-(2,3,4,5-tetrahydro-3-oxopyridazin-6-yl)-3-methoxycarbonyl-3-methyl-1H-indolin-2-one in a yield of 58% of theory; m.p. 272°–273° C., after recrystallisation from methanol.

The starting material, 3-methoxycarbonyl-3-methyl-5-(3-methoxycarbonylpropionyl)-1H-indolin-2-one (m.p. 148°–150° C.) is obtained, analogously to the precursor of Example 1, from 3-methoxycarbonyl-3-methyloxindole in a yield of 45% of theory.

EXAMPLE 3

5-(2,3,4,5-Tetrehydro-3-oxopyridazin-6-yl)-3-isopropyloxycarbonyl-3-methyl-1H-indolin-2-one 3.2 g. (10 mMole) 5-(2,3,4,5-tetrahydro-3-oxo-pyridazin-6-yl)-3-ethoxycarbonyl-3-methyl-1H-indolin-2-one (compound of Example 1) are added to a solution of 1.0 g. of sodium in 60 ml. isopropanol, heated under reflux for 1 hour, acidified by the addition of an ethanolic solution of hydrogen chloride, evaporated in a vacuum and the residue taken up in water and dichloromethane, filtered, the organic phase evaporated, combined with the filter residue and chromatographed on silica gel (elution agent: 1,1,1-trichloroethane/isopropanol 9:1 v/v). There is isolated 1.8 g. of the title compound (55% of theory); m.p. 290°–291° C., after recrystallisation from diethyl ether.

EXAMPLE 4

5-(2,3-Dihydro-3-oxopyridazin-6-yl)-3-ethoxycarbonyl-3-methyl-1H-indolin-2-one

A solution of 2.0 g. (6.3 mMole) 5-(2,3,4,5-tetrahydro-3-oxopyridazin-6-yl)-3-ethoxycarbonyl-3-methyl-1H-indolin-2-one (compound of Example 1) in 300 ml. dioxan is stirred with 34 g. pyrolusite for 48 hours at 90° C. The reaction mixture is filtered, then washed with dichloromethane and methanol, the filtrate evaporated and the residue triturated with diethyl ether. There is obtained 0.8 g of the title compound (41% of theory); m.p. 289°–291° C.

EXAMPLE 5

5-(2,3,4,5-Tetrahydro-3-oxopyridazin-6-yl)-3-propyl-3-ethoxycarbonyl-1H-indolin-2-one In a manner analogous to that described in Example 1, the title compound is obtained in a yield of 35% of theory; m.p. 190°–192° C., after recrystallisation from diethyl ether.

The starting material, 3-methoxycarbonyl-3-propyl-5-(3-methoxycarbonylpropionyl)-1H-indolin-2-one, can be prepared as follows:

(a) A solution of 48 g. (0.17 mole) diethyl 2-(2-nitrophenyl)-malonate in 33 ml. 1-iodopropane is mixed with a solution of 5.3 g. sodium in 600 ml. ethanol, heated under reflux overnight, evaporated and the residue mixed with water and extracted with diethyl ether. After evaporating the extract, there are obtained 48 g. (88% of theory) diethyl 2-(2-nitrophenyl)-2-propylmalonate as crude product.

(b) 48 g. of the compound obtained in (a) are dissolved in 800 ml. ethanol and hydrogenated over 12 g. Raney nickel at a hydrogen pressure of 4 bar. The reaction mixture is filtered, the filtrate is evaporated and the residue is chromatographed over silica gel, eluting with 1,1,1-trichloroethane, to give 20.1 g. 3-ethoxycarbonyl-3-propyl-1H-indolin-2-one (55% of theory); m.p. 91°–93° C., after recrystallisation from ligroin.

(c) Analogously to the precursor of Example 1, 3-ethoxycarbonyl-3-propyl-5-(3-methoxycarbonylpropionyl)-1H-indolin-2-one is obtained in the form of an oil from the intermediate product described in (b).

Male Sprague-Dawley rats weighing between 350 and 450 g were narcotized by intraperitoneal injection of a barbiturate and fitted with instrumentation for the examinations as follows:

A pressure measuring catheter (Miller Mikrotip/-diameter 0.5 mm) was inserted through the arteria carotis dextra into the left ventricle. The pressure inside the left ventricle was continually registered through this catheter. The signal from this Mikrotip was electronically differentiated and $(dp/dt)_{60}$—the slope of the pressure-time curve at a pressure of 60 mmHg—was taken as a measure for the inotropy.

A polypropylene catheter was bound in a vena jugularis for the intravenous injection of the test substances.

A further polypropylene catheter was inserted through an arteria femoralis into the abdominal aorta for the direct measurement of the arterial blood pressure.

The ECG was traced with subcutaneous insertion electrodes.

During the preparation of the animal and during the entire test period the rats were fixed on an electronically heated and thermostatically controlled operating table.

The test substances were always introduced by intravenous injection, with an injection volume, per injection, of 1 ml/kg body weight. In intervals of 10 min each, doses increasing from 0.01 to 30 mg of the test substances were intravenously injected. In this way dose effect curves for the measured parameters for the investigated substances were obtained.

From the measured data, using a regression calculation, equipotent doses for the positively inotropic effect $(dp/dt)_{60}$ were calculated. In addition, as criterion for the effectiveness of the substances, the maximum effect obtained (maximal increase of $(dp/dt)_{60}$ and its corresponding dose were determined. The table that follows reports the equipotent doses ($ED_{1,5}$=the dose in mg/kg that leads to an increase of $(dp/dt)_{60}$ of 1.5 mHg/sec) and the maximal effectiveness ($W_{max}$=the maximal increase of $(dp/dt)_{60}$) and the dose producing the maximum effectiveness.

TABLE

| Compound from | $ED_{1,5}$ mHg/sec | $W_{max}$ Δ mHg/sec | mg/kg i. V. |
|---|---|---|---|
| Example 1 | 0,049 | 2,7 | 0,3 |

I claim:
1. Heterocyclic substituted indolinone of the formula:

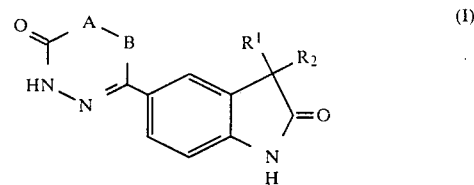

wherein $R_1$ is a hydrogen atom, an alkyl radical or a hydroxyalkyl radical, $R_2$ is a carboxyl group, an alkoxycarbonyl radical, a hydroxyalkyl radical or an alkylcarbonyloxyalkyl radical or $R_1$ and $R_2$, together with the carbon atom to which they are attached, form a lactone having 4, 5 or 6 ring atoms, derived from compounds wherein $R_1$ is hydroxyalkyl and $R_2$ is carboxyl, A–B is —CH$_2$—CH(R$_3$)—, or —CH=CR$_3$— radical, $R_3$ being a hydrogen atom or an alkyl or hydroxyalkyl radical, wherein the alkyl groups independently contain 1 to 6 carbon atoms; as well as the tautomers thereof and the physiologically acceptable acid salts thereof.

2. Compound of claim 1 wherein $R_1$ is $C_1$–$C_3$ alkyl, $R_2$ is ($C_1$–$C_4$-alkoxy)carbonyl, hydroxy ($C_1$–$C_2$ alkyl) or ($C_1$–$C$ alkyl)carbonyloxy ($C_1$–$C_2$ alkyl) or $R_1$ and $R_2$ together with the carbon atom to which they are attached form a five-membered lactone ring, A–B is —CH$_2$—CHR$_3$— or —CH=CH—, wherein $R_3$ is a hydrogen atom or $C_1$–$C_2$ alkyl or hydroxy ($C_1$–$C_2$ alkyl).

3. The compound of claim 1 wherein $R_1$ is methyl or propyl, $R_2$ is methoxycarbonyl, ethoxycarbonyl, isopropyloxycarbonyl, tert-butyloxycarbonyl, hydroxymethyl or methylcarbonyloxymethyl or $R_1$ and $R_2$ together with the carbon atom to which they are attached form a five-membered lactone ring, A-B is —CH$_2$—CHR$_3$— or —CH=CH—, wherein $R_3$ is a hydrogen atom or a methyl or hydroxymethyl radical.

4. The compound of claim 1 wherein $R_1$ is methyl or propyl.

5. The compound of claim 1 wherein $R_2$ is methoxycarbonyl, ethoxycarbonyl, isopropyloxycarbonyl, tert-butyloxycarbonyl, hydroxymethyl or methylcarbonyloxymethyl.

6. The compound of claim 1 wherein $R_1$ and $R_2$ together with the carbon atom to which they are attached form a γ-butyrolactone ring.

7. The compound of claim 1 wherein A-B is —CH$_2$—CH$_2$—, —CH=CH—, —CH$_2$—CH(CH$_3$)—, or —CH$_2$—CH(CH$_2$OH)—.

8. The compound of claim 1 wherein the compound is 5-(2,3,4,5-tetrahydro-3-oxopyridazin-6-yl)-3-ethoxycarbonyl-3-methyl-1H-indolin-2-one.

9. Pharmaceutical composition for reducing blood pressure, producing a positive inotropic action, decreasing thrombocyte aggregation and/or improving microcirculation comprising an effective amount of at least one compound of claim 1, in admixture with a pharmaceutically acceptable carrier.

10. A method of reducing blood pressure in a patient in need of such reduction, said method comprising administering to said patient an anti-hypertensive effective amount of a compound of claim 1.

11. Method of producing a positive inotropic action in a patient in need of such action, said method comprising administering to said patient an effective amount of a compound of claim 1.

12. A method of decreasing thrombocyte aggregation in a patient in need of such decrease, said method comprising administering to said patient an effective amount of a compound of claim 1.

13. A method of improving microcirculation in a patient in need of such improvement, said method comprising administering to said patient an effective amount of a compound of claim 1.

* * * * *